United States Patent [19]

Fahmy

[11] 4,362,723
[45] * Dec. 7, 1982

[54] S-ARYL S-(TERTIARY ALKYL) ALKYLPHOSPHONODITHIOATE INSECTICIDES AND NEMATOCIDES

[75] Inventor: Mohamed A. Fahmy, Princeton, N.J.

[73] Assignee: Rhone-Poulenc Agrochimie, Lyons, France

[*] Notice: The portion of the term of this patent subsequent to Aug. 18, 1998, has been disclaimed.

[21] Appl. No.: 221,643

[22] Filed: Dec. 31, 1980

[51] Int. Cl.$^3$ ...................... A01N 57/022; C07F 9/40
[52] U.S. Cl. .................................... 424/222; 260/961
[58] Field of Search ........................ 260/961; 424/222

[56] References Cited
U.S. PATENT DOCUMENTS 3,209,020  9/1965  Schrader ............................ 260/941
3,705,216 12/1972  Farley ............................... 260/941
4,284,626  8/1981  Fahmy ............................... 260/961

Primary Examiner—Anton H. Sutto

Attorney, Agent, or Firm—Burns, Doane, Swecker & Mathis

[57] ABSTRACT

Compounds having the formula

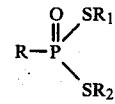

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;
$R_1$ is aryl;
$R_2$ is tertiary alkyl of 4 to 8 carbon atoms; are disclosed as well as their use as insecticides and nematocides, e.g., in controlling Corn rootworm and Southern Armyworm.

16 Claims, No Drawings

S-ARYL S-(TERTIARY ALKYL) ALKYLPHOSPHONODITHIOATE INSECTICIDES AND NEMATOCIDES

CROSS-REFERENCE TO RELATED APPLICATIONS

An application entitled "O-ARYL S-BRANCHED ALKYL ALKYLPHOSPHONODITHIOATE INSECTICIDES AND NEMATOCIDES", Ser. No. 108,329, filed Dec. 31, 1979 in the name of Mohamed A. Fahmy, (now U.S. Pat. No. 4,284,626) discloses certain O-aryl S-branched alkyl alkylphosphonodithioates. An application entitled "O-ARYL S-(TERTIARY ALKYL) ALKYLPHOSPHONOTHIOATE INSECTICIDES AND NEMATOCIDES", (Ser. No. 209,094), filed Nov. 21, 1980, now abandoned, in the name of Mohamed A. Fahmy discloses certain O-aryl S-(tertiary alkyl) alkylphosphonothioate insecticides and nematocides.

SUMMARY OF THE INVENTION

This invention relates to S-aryl S-(tertiaryalkyl) alkylphosphonodithioate compounds and their use as insecticides and nematocides.

More particularly, the compounds of the invention have the formula:

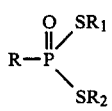

in which R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is aryl; and
$R_2$ is tertiary alkyl of 4 to 8 carbon atoms.

These compounds exhibit a wide range of insecticidal and nematocidal activity and are of particular interest in controlling Corn rootworm because of their excellent activity against this pest and their long residual soil activity.

DETAILED DESCRIPTION OF THE INVENTION

An important structural feature of the compounds of this invention is that $R_2$ in the above formula is tertiary alkyl. A variety of S-aryl S-alkyl alkylphosphonodithioate insecticides are known in the art, such as in U.S. Pat. No. 3,209,020. However, applicant is aware of none which correspond to the above formula where $R_2$ is tertiary alkyl.

It has been found that the branched compounds of this invention possess unexpected advantageous properties. For example, they exhibit excellent stability and long residual activity particularly in soil. Since the activity of the tertiary compounds against Corn rootworm is good and residual activity in soil is long, the compounds of this invention are of special interest for controlling Corn rootworm.

The compounds disclosed herein can be prepared by the methods known to those in the art. Preferably, the compounds of this invention are prepared from a starting material which is S-(tertiary-alkyl) alkylphosphonothioic halide, the preparation of which is illustrated in Example 1.

The preferred reaction scheme is as follows:

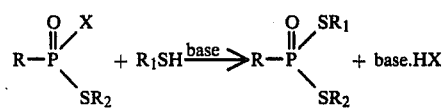

in which R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;
$R_1$ is aryl;
$R_2$ is tertiary alkyl of 4 to 8 carbon atoms; and
X is halogen, preferably Cl.

Suitable aryl groups include phenyl and phenyl substituted with one or more alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, or trifluoromethyl, or combinations of the foregoing.

The tertiary alkyl group is preferably tert-butyl or tert-amyl.

The reaction is advantageously carried out at a temperature of about 0° C. to 100° C. in an organic solvent in the presence of a tertiary amine, aqueous base, such as aqueous NaOH, or by producing the alkali salt of the thiophenol using alkali metal salts such as sodium ethoxide.

Suitable organic solvents are, for example, benzene, toluene, cyclohexane and 2-butanone.

Suitable tertiary amines include trimethylamine, triethylamine, dimethylaniline, diethylaniline and pyridine.

The alkylphosphonothioate compounds of this invention are effective as insecticides and/or nematocides at low concentrations. Because of the small amounts of the compounds required for effective control, it is generally impractical to apply the compounds directly as such. Therefore, it is desirable that the compounds be applied in the form of liquid compositions, or in combination with other vehicles or extenders.

The compositions containing the active compounds of this invention can be dispersions or emulsions. Since the active compounds are substantially water insoluble, it is desirable to add a small amount of an inert, non-phytotoxic organic solvent which can be readily dispersed in an aqueous medium to produce a uniform dispersion of the active component. For example, an effective liquid composition can be prepared with the active component, acetone or ethanol, water, and a surface-active agent such as Tween-20 (polyoxyethylene sorbitan monolaurate) or any of the other well known surface-active agents.

The compositions containing the active compounds can also be in powdered or granular form. For example, the active compound can be mixed with a suitable solid carrier such as kaolinite, bentonite, talc or the like, in amounts of about 5% to 20% by weight.

For the control of insects, the active ingredients are used at concentrations of from 0.01% to about 1% by weight of the total formulation. As nematocides, the active component is effective within the range of about 0.5 to 5 kg/hectare. Under ideal conditions, depending on the pest to be controlled, the lower rate may offer adequate protection. On the other hand, adverse weather conditions, resistence of the pest and other factors may require that the active ingredient be used in higher proportions.

When the pest is soil-borne, the formation containing the active ingredient is distributed evenly over the area to be treated in any convenient manner. The active component can be washed into the soil by spraying with water over the area or can be left to the natural action of rainfall. After application, the formulation can be distributed in the soil by plowing or disking. Application can be prior to planting or after planting but before sprouting has taken place or after sprouting.

The following examples illustrate the preparation of the compounds of this invention and their pesticidal properties. It will be understood that all of the compounds disclosed herein can be prepared by methods analogous to those described below.

EXAMPLE 1

S-tert-butyl ethylphosphonothioic chloride

To a solution of ethylphosphonic dichloride (32.0 g, 0.22 mol) in 300 ml toluene, was added 2-methyl-2-propanethiol (18 g, 0.2 mol). While stirring triethylamine (22 g, 0.22 mol) was added dropwise and the temperature of the reaction was maintained at 30°–35° C. during the addition of the amine. After the complete addition of the amine, the mixture was stirred overnight at room temperature. The amine hydrochloride was filtered and the toluene solution was concentrated under vacuum. Hexane (200 ml) was added and the solution was filtered again.

The solvents were stripped off under vacuum and the residual liquid was distilled. The product (25 g, 72.5% yield) distilled at 72–73 C./0.7 mm. $^1$H-NMR in chloroform-d-Si(Me)$_4$ confirmed the structure of the title compound.

EXAMPLE 2

Preparation of S-phenyl S-tert-butyl ethylphosphonodithioate

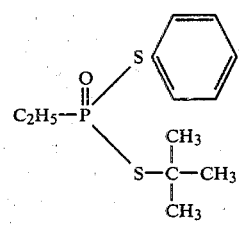

To a solution of S-tert butyl ethylphosphonothioic chloride (5 g, 0.025 mol), and thiophenol (3.0 g, 0.027 mol) in 20 ml acetone, was added, in one portion, triethylamine (3.0 g, 0.027 mol). The mixture was stirred overnight under nitrogen at room temperature. The reaction mixture was diluted with toluene (100 ml) and washed three times with 5% NaOH solution, and twice with water. The solution was dried over anhydrous sodium sulfate and the solvent was stripped off under vacuum. The residual liquid was subjected to high vacuum (0.2 mm) at 60° C. to yield the desired product as confirmed by $^1$H-NMR spectrum in chloroform-d-SiMe$_4$.

EXAMPLE 3

In a manner analogous to that of Example 2, the compound S-(p-chlorophenyl S-tert-butyl ethylphosphonodithioate was prepared.

EXAMPLE 4

Testing for Corn rootworm intrinsic activity, and activity against Southern Armyworm.

A. Corn Rootworm Intrinsic Activity (CRW)

The test compound is prepared in a one percent solution with acetone or ethanol. The stock solution is then diluted with an aqueous solution of Tween-20 and water to the appropriate concentration (i.e., 500, 100, 1, 0.1, or 0.05 ppm). Two ml of this solution is pipetted into a 9 cm petri dish containing two layers of filter paper. Second instar larvae are introduced and the dish closed. Observations for mortality and moribund larvae are made after two days (48 hours) exposure. Insecticidal activity is primarily contact and vapor action with minimum ingestion. The results are tabulated in Table 1.

B. Southern Armyworm Intrinsic Activity (SAW)

Stock solution (1%) of test material was made in acetone and diluted to the desired concentration by a 500 ppm Tween-20 aqueous solution. Lima bean leaves are dipped into the solution and transferred to petri dishes (100 × 15 mm) containing two filter papers moistened with 2 ml water. Each petri dish contained one leaf and was kept open to dry out the solution on the leaf. Five third instar larvae of Southern Armyworm (*Spodoptera eridania*) were added to the leaf and the dish was finally covered.

The insects were held at 78° F. for 72 hours and percent kill was recorded. The results are tabulated in Table 1.

TABLE 1

| Example | % Kill SAW | | CRW | | |
|---|---|---|---|---|---|
| | Rate (ppm) | | | | |
| | 500 | 100 | 1 | 0.1 | 0.05 |
| 2 | 100 | 10 | 100 | 100 | 55 |
| 3 | 100 | 90 | 100 | 10 | — |

Although the present invention has been described with specific embodiments, it is to be understood that modifications and variations can be made without departing from the spirit and scope of this invention defined in the appended claims, as those skilled in the art will readily understand.

I claim:

1. A method for controlling insects or nematodes which comprises applying thereto or to their habitat, in an amount pesticidal to said insects or nematodes, a compound of the formula

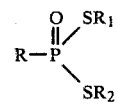

in which
R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;

R₁ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and R₂ is tertiary alkyl of 4 to 8 carbon atoms.

2. A method for controlling Corn rootworm which comprises providing in the soil, in an amount pesticidal to Corn rootworm, a compound of the formula

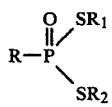

in which

R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms, or haloalkynyl of 2 to 8 carbon atoms;

R₁ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano and trifluoromethyl; and R₂ is tertiary alkyl of 4 to 8 carbon atoms.

3. The method of claim 2 in which R₁ is phenyl.

4. The method of claim 2 in which R is alkyl of 1 to 8 carbon atoms.

5. The method of claim 2 in which R is methyl or ethyl; and

R₂ is tert-butyl or tert-amyl.

6. The method of claim 2 in which

R is methyl or ethyl;

R₁ is phenyl; and

R₂ is tert-butyl or tert-amyl.

7. A compound of the formula

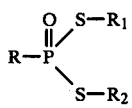

in which

R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;

R₁ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and R₂ is tertiary alkyl of 4 to 8 carbon atoms.

8. A compound of claim 7 in which R₁ is phenyl.

9. A compound of claim 7 in which R₂ is tert-butyl or tert-amyl.

10. A compound of claim 7 in which R is alkyl of 1 to 8 carbon atoms.

11. A compound of claim 7 in which

R is methyl or ethyl;

R₁ is phenyl; and

R₂ is tert-butyl or tert-amyl.

12. A compound of claim 7 in which

R is ethyl;

R₁ is phenyl; and

R₂ is tert-butyl.

13. A compound of claim 7 in which R₂ is tert-butyl.

14. A compound of claim 7 in which R is ethyl.

15. A composition for use in controlling insects or nematodes comprising, as the active ingredient, a compound of the formula

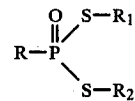

in which

R is alkyl of 1 to 8 carbon atoms, haloalkyl of 1 to 8 carbon atoms, alkenyl of 2 to 8 carbon atoms, haloalkenyl of 2 to 8 carbon atoms, alkynyl of 2 to 8 carbon atoms or haloalkynyl of 2 to 8 carbon atoms;

R₁ is phenyl or phenyl substituted with 1 or more members selected from the group consisting of alkyl of 1 to 4 carbon atoms, alkoxy of 1 to 4 carbon atoms, alkylthio of 1 to 4 carbon atoms, alkylsulfinyl of 1 to 4 carbon atoms, alkylsulfonyl of 1 to 4 carbon atoms, Cl, Br, F, nitro, cyano, and trifluoromethyl; and R₂ is tertiary alkyl of 4 to 8 carbon atoms, in an amount effective as an insecticide or nematocide; and an inert, non-phytotoxic organic solvent or solid carrier.

16. The composition of claim 15 in which R₂ is tert-butyl or tert-amyl.

* * * * *